(12) United States Patent
Berman et al.

(10) Patent No.: US 6,424,849 B1
(45) Date of Patent: *Jul. 23, 2002

(54) SELF-CONTAINED METHOD FOR DETERMINING BLOOD GLUCOSE LEVELS FROM AN IR BEAM REFLECTED FROM THE SURFACE OF THE SKIN

(75) Inventors: Herbert L. Berman, Los Altos Hills; Jeffrey N. Roe, San Ramon, both of CA (US)

(73) Assignee: MedOptix, Inc., Cupertino, CA (US)

( * ) Notice: Subject to any disclaimer, the term of this patent is extended or adjusted under 35 U.S.C. 154(b) by 21 days.

This patent is subject to a terminal disclaimer.

(21) Appl. No.: 09/668,848

(22) Filed: Sep. 22, 2000

Related U.S. Application Data

(63) Continuation of application No. 09/547,433, filed on Apr. 12, 2000, which is a continuation-in-part of application No. PCT/US99/23823, filed on Oct. 12, 1999.
(60) Provisional application No. 60/103,883, filed on Oct. 13, 1998.

(51) Int. Cl.$^7$ ................................................ A61R 5/00
(52) U.S. Cl. ...................... 600/316; 600/322; 600/365; 600/473
(58) Field of Search ................................ 600/309–310, 600/322–324, 316, 365, 473

(56) References Cited

U.S. PATENT DOCUMENTS

| | | | |
|---|---|---|---|
| 4,151,001 A | | 4/1979 | Anderson, Jr. et al |
| 5,113,860 A | | 5/1992 | McQuinn |
| 5,370,114 A | * | 12/1994 | Wong et al. ................. 600/322 |

(List continued on next page.)

FOREIGN PATENT DOCUMENTS

| | | |
|---|---|---|
| EP | 0 404 562 | 12/1990 |
| JP | 7-184883 | 7/1995 |
| WO | WO 00/21437 | 4/2000 |

OTHER PUBLICATIONS

Bhandare, P. et al. (1993). "Multivariate Determination of Glucose in Whole Blood Using Partial Least–Squares and Artificiatl Neural Networks Based on Mid–Infrared Spectroscopy," *Appl. Spectr.* 47(8):1214–1221.

Heise, H.M. et al. (1989). "Multivariate Determination of Glucose in Whole Blook by Attenuated Total Reflection Infrared Spectroscopy," *Anal Chem.* 61:2009–2015.

Hiese, H.M. et al. (1998), "Clinical Chemistry and Near Infrared Spectroscopy: Technology for Non–Invasive Glucose Monitoring," *J. Near Infrared Spectrosc.* 6:349–359.

Kajiwara, K. et al. (1992). "Spectroscopic Quantitative Analysis of Blood Glucose by Fourier Transform Infrared Spectroscopy with an Attenuated Total Reflection Prism," *Med. Prog. through Tech.* 18:181–189.

(List continued on next page.)

*Primary Examiner*—Eric F. Winakur
*Assistant Examiner*—Matthew Kremer
(74) *Attorney, Agent, or Firm*—Morrison & Foerster LLP

(57) ABSTRACT

This involves a non-invasive glucose measurement device and a process for determining blood glucose level in the human body using the device. In typical operation, the glucose measurement device is self-normalizing in that it does not employ an independent reference sample in its operation. The device uses attenuated total reflection (ATR) infrared spectroscopy. Preferably, the device is used on a fingertip and compares two specific regions of a measured infrared spectrum to determine the blood glucose level of the user. Clearly, this device is especially suitable for monitoring glucose levels in the human body, and is especially beneficial to users having diabetes mellitus. The device and procedure may be used for other analyte materials which exhibit unique mid-IR signatures of the type described herein and that are found in appropriate regions of the outer skin.

12 Claims, 9 Drawing Sheets

U.S. PATENT DOCUMENTS

| | | | |
|---|---|---|---|
| 5,408,312 A | | 4/1995 | Pries et al. |
| 5,410,471 A | * | 4/1995 | Alyfuku et al. ............. 600/300 |
| 5,429,128 A | | 7/1995 | Cadell et al. |
| 5,452,716 A | * | 9/1995 | Clift ........................... 600/373 |
| 5,582,184 A | | 12/1996 | Erickson et al. |
| 5,655,530 A | | 8/1997 | Messerschmidt |
| 5,682,233 A | | 10/1997 | Brinda |
| 5,722,397 A | | 3/1998 | Eppstein |
| 5,749,217 A | | 5/1998 | Etheridge |
| 5,765,717 A | | 6/1998 | Gottselig |
| 5,817,605 A | | 10/1998 | Papay |
| 5,820,570 A | | 10/1998 | Erickson et al. |
| 5,879,310 A | | 3/1999 | Sopp et al. |
| 5,879,367 A | | 3/1999 | Latterell et al. |
| 5,900,632 A | | 5/1999 | Sterling et al. |
| 5,935,062 A | | 8/1999 | Messerschmidt et al. |
| 6,026,314 A | * | 2/2000 | Amerov et al. ............. 600/322 |
| 6,128,091 A | | 10/2000 | Uchida et al. |
| 6,172,743 B1 | | 1/2001 | Kley et al. |
| 6,205,272 B1 | | 3/2001 | O'Rourke et al. |

OTHER PUBLICATIONS

Klonoff, D.C. (Mar. 1997), "Noninvasive Blood Glucose Monitoring," *Diabetes Care* 20(3):433–437.

Kruse–Jarres J.D. et al. (Feb. 1990). "Glucose and Other Constituents of Blood Determined by ATR–FTIR–Spectroscopy," *Clin. Chem.* 36(2):401–402.

Mak, V.H. et al. (Aug. 1990). "Pecutaneous Penetration Enhancement in Vivo Measured by Attenuated Total Refelectance Infrared Spectroscopy," *Pharm. Res.* 7(8):835–841.

Mendelson, Y. et al. (1990). "Blood Glucose Measurement by Multiple Attenuated Total Reflection and Infrared Absorption Spectroscopy," *IEEE Trans. Biomed. Engin.* 37(5):458–465.

Potts, R.O. et al. (1985). "A Noninvasive, In Vivo Technique to Quantitatively Measure Water Concentration of the Stratum Corneum Using Attenuated Total–Reflectance Infrared Spectroscopy," *Arch. Dermatol. Res.* 277(6):489–495.

Rao, G. (Dec. 1993). "Reverse Iontophoresis: Development of a Noninvasive Approach for Glucose Monitoring," *Pharm Res.* 10(12):1751–1755.

Isojima, K. et al., (2000) "Application of Infrared Attenuated Total Reflection Microspectroscopy to Diagnosis of Arterriosclerosis and Diabetes" *Proceedings of the Symposium on Electrical and Electronic Insulating Materials and Applications in Systems*, 32:293–296 and English translation.

Kanazawa, M. (1997) "Determination of Blood Glucose Level with Infrared Spectroscopy" *Nihon Bunko Gakkai Igaku Seibutsugaku Kenkyu Bukai Shinpojiumu Tekisuto*, 1997:26–30 with English translation.

* cited by examiner

SELF-CONTAINED METHOD FOR DETERMINING BLOOD GLUCOSE LEVELS FROM AN IR BEAM REFLECTED FROM THE SURFACE OF THE SKIN

RELATED APPLICATIONS

This application is a continuation of U.S. application Ser. No. 09/547,433, entitled "Infrared ATR glucose measurement system (II)", filed on Apr. 12, 2000, which was a continuation-in-part of PCT/US99/23823, filed Oct. 12, 1999, designating the U.S., which in turn derives benefit from U.S. App. Ser. No. 60/103,883, to Berman and Roe, filed Oct. 13, 1998.

FIELD OF THE INVENTION

This invention involves a non-invasive glucose measurement device and a process for determining blood glucose level in the human body using the device. In typical operation, the glucose measurement device is self-normalizing in that it does not employ an independent reference sample in its operation. The inventive device uses attenuated total reflection (ATR) infrared spectroscopy. Preferably, the device is used on a fingertip or other part of the body. Although the inventive procedure preferably compares two specific regions of a measured mid-infrared spectrum to determine the blood glucose level of the user. Clearly, this device is especially suitable for monitoring glucose levels in the human body, and is especially beneficial to users having diabetes mellitus. The device and procedure may be used for other materials which exhibit unique mid-IR signatures of the type described below and that are found in appropriate regions of the outer skin. A cleaning kit and related procedure for preparation of the skin surface is also included.

BACKGROUND OF THE INVENTION

The American Diabetes Association reports that nearly 6% of the population in the United States, a group of 16 million people, has diabetes. The Association further reports that diabetes is the seventh leading cause of death in the United States, contributing to nearly 200,000 deaths per year. Diabetes is a chronic disease having no cure. The complications of the disease include blindness, kidney disease, nerve disease, and heart disease, perhaps with stroke. Diabetes is said to be the leading cause of new cases of blindness in individuals in the range of ages between 20 and 74; from 12,000–24,000 people per year lose their sight because of diabetes. Diabetes is the leading cause of end-stage renal disease, accounting for nearly 40% of new cases. Nearly 60–70% of people with diabetes have mild to severe forms of diabetic nerve damage which, in severe forms, can lead to lower limb amputations. People with diabetes are 2–4 times more likely to have heart disease and to suffer strokes.

Diabetes is a disease in which the body does not produce or properly use insulin, a hormone needed to convert sugar, starches, and the like into energy. Although the cause of diabetes is not completely understood, genetics, environmental factors, and viral causes have been partially identified.

There are two major types of diabetes: Type I and Type II. Type I diabetes (formerly known as juvenile diabetes) is an autoimmune disease in which the body does not produce any insulin and most often occurs in young adults and children. People with Type I diabetes must take daily insulin injections to stay alive.

Type II diabetes is a metabolic disorder resulting from the body's inability to make enough, or properly to use, insulin. Type II diabetes accounts for 90–95% of diabetes. In the United States, Type II diabetes is nearing epidemic proportions, principally due to an increased number of older Americans and a greater prevalence of obesity and a sedentary lifestyle.

Insulin, in simple terms, is the hormone that unlocks the cells of the body, allowing glucose to enter those cells and feed them. Since, in diabetics, glucose cannot enter the cells, the glucose builds up in the blood and the body's cells literally starve to death.

Diabetics having Type I diabetes typically are required to self-administer insulin using, e.g., a syringe or a pin with needle and cartridge. Continuous subcutaneous insulin infusion via implanted pumps is also available. Insulin itself is typically obtained from pork pancreas or is made chemically identical to human insulin by recombinant DNA technology or by chemical modification of pork insulin. Although there are a variety of different insulins for rapid-, short-, intermediate-, and long-acting forms that may be used variously, separately or mixed in the same syringe, use of insulin for treatment of diabetes is not to be ignored.

It is highly recommended by the medical profession that insulin-using patients practice self-monitoring of blood glucose (SMBG). Based upon the level of glucose in the blood, individuals may make insulin dosage adjustments before injection. Adjustments are necessary since blood glucose levels vary day to day for a variety of reasons, e.g., exercise, stress, rates of food absorption, types of food, hormonal changes (pregnancy, puberty, etc.) and the like. Despite the importance of SMBG, several studies have found that the proportion of individuals who self-monitor at least once a day significantly declines with age. This decrease is likely due simply to the fact that the typical, most widely used, method of SMBG involves obtaining blood from a finger stick. Many patients consider obtaining blood to be significantly more painful than the self-administration of insulin.

There is a desire for a less invasive method of glucose measurement. Methods exist or are being developed for a minimally invasive glucose monitoring, which use body fluids other than blood (e.g., sweat or saliva), subcutaneous tissue, or blood measured less invasively. Sweat and saliva are relatively easy to obtain, but their glucose concentration appears to lag in time significantly behind that of blood glucose. Measures to increase sweating have been developed and seem to increase the timeliness of the sweat glucose measurement, however.

Subcutaneous glucose measurements seem to lag only a few minutes behind directly measured blood glucose and may actually be a better measurement of the critical values of glucose concentrations in the brain, muscle, and in other tissue. Glucose may be measured by non-invasive or minimally-invasive techniques, such as those making the skin or mucous membranes permeable to glucose or those placing a reporter molecule in the subcutaneous tissue. Needle-type sensors have been improved in accuracy, size, and stability and may be placed in the subcutaneous tissue or peripheral veins to monitor blood glucose with small instruments. See, "An Overview of Minimally Invasive Technologies", Clin. Chem. 1992 September; 38(9):1596–1600.

Truly simple, non-invasive methods of measuring glucose are not commercially available.

U.S. Pat. No. 4,169,676 to Kaiser, shows a method for the use of ATR glucose measurement by placing the ATR plate directly against the skin and especially against the tongue. The procedure and device shown there uses a laser and determines the content of glucose in a specific living tissue sample by comparing the IR absorption of the measured material against the absorption of IR in a control solution by use of a reference prism. See, column 5, lines 31 et seq.

Swiss Patent No. 612,271, to Dr. Nils Kaiser, appears to be the Swiss patent corresponding to U.S. Pat. No. 4,169,676.

U.S. Pat. No. 4,655,255, to Dähne et al., describes an apparatus for non-invasively measuring the level of glucose in a blood stream or tissues of patients suspected to have diabetes. The method is photometric and uses light in the near-infrared region. Specifically, the procedure uses light in the 1,000 to 2,500 nm range. Dähne's device is jointly made up to two main sections, a light source and a detector section. They may be situated about a body part such as a finger. The desired near-infrared light is achieved by use of filters. The detector section is made up of a light-collecting integrating sphere or half-sphere leading to a means for detecting wavelengths in the near-infrared region. Dähne et al. goes to some lengths teaching away from the use of light in the infrared range having a wavelength greater than about 2.5 micrometers since those wavelengths are strongly absorbed by water and have very little penetration capability into living tissues containing glucose. That light is said not to be "readily useable to analyze body tissue volumes at depths exceeding a few microns or tens of microns."Further, Dähne et al. specifically indicates that an ATR method which tries to circumvent the adverse consequences of the heat effect by using a total internal reflection technique is able only to investigate to tissue depths not exceeding about 10 micrometers, a depth which is considered by Dähne et al. to be "insufficient to obtain reliable glucose determination information."

U.S. Pat. No. 5,028,787, to Rosenthal et al., describes a non-invasive glucose monitoring device using near-infrared light. The light is passed into the body in such a way that it passes through some blood-containing region. The so-transmitted or reflected light is then detected using an optical detector. The near-infrared light sources are preferably infrared emitting diodes (IRED). U.S. Pat. No. 5,086,229 is a continuation in part of U.S. Pat. No. 5,028,787.

U.S. Pat. No. 5,178,142, to Harjunmaa et al, teaches the use of a stabilized near-infrared radiation beam containing two alternating wavelengths in a device to determine a concentration of glucose or other constituents in a human or animal body. Interestingly, one of the transmitted IR signals is zeroed by variously tuning one of the wavelengths, changing the extracellular to intracellular fluid ratio of the tissue by varying the mechanical pressure on a tissue. Or, the ratio may be allowed to change as a result of natural pulsation, e.g., by heart rate. The alternating component of the transmitted beam is measured in the "change to fluid ratio" state. The amplitude of the varying alternating signal is detected and is said to represent glucose concentration or is taken to represent the difference in glucose concentration from a preset reference concentration.

U.S. Pat. No. 5,179,951 and its divisional, U.S. Pat. No. 5,115,133, to Knudson, show the application of infrared light for measuring the level of blood glucose in blood vessels in the tympanic membrane. The detected signal is detected, amplified, decoded, and, using a microprocessor, provided to a display device. The infrared detector (No. 30 in the drawings) is said simply to be a "photo diode and distance signal detector" which preferably includes "means for detecting the temperature of the volume in the ear between the detector and the ear's tympanic membrane." Little else is said about the constituency of that detector.

U.S. Pat. No. 5,433,197, to Stark, describes a non-invasive glucose sensor. The sensor operates in the following fashion. A near-infrared radiation is passed into the eye through the cornea and the aqueous humor, reflected from the iris or the lens surface, and then passed out through the aqueous humor and cornea. The reflected radiation is collected and detected by a near-infrared sensor which measures the reflected energy in one or more specific wavelength bands. Comparison of the reflected energy with the source energy is said to provide a measure of the spectral absorption by the eye components. In particular, it is said that the level of glucose in the aqueous humor is a function of the level of glucose in the blood. It is said in Stark that the measured glucose concentration in the aqueous humor tracks that of the blood by a fairly short time, e.g., about 10 minutes. The detector used is preferably a photodiode detector of silicon or InGaAs. The infrared source is said preferably to be an LED, with a refraction grating so that the light of a narrow wavelength band, typically 10 to 20 nanometers wide, passes through the exit slit. The light is in the near-infrared range. The use of infrared regions below 1400 nanometers and in the region between 1550 and 1750 nanometers is suggested.

U.S. Pat. No. 5,267,152, to Yang et al., shows a non-invasive method and device for measuring glucose concentration. The method and apparatus uses near-infrared radiation, specifically with a wavelength of 1.3 micrometers to 1.8 micrometers from a semiconductor diode laser. The procedure is said to be that the light is then transmitted down through the skin to the blood vessel where light interacts with various components of the blood and is then diffusively reflected by the blood back through the skin for measurement.

Similarly, U.S. Pat. No. 5,313,941, to Braig et al., suggests a procedure and apparatus for monitoring glucose or ethanol and other blood constituents in a non-invasive fashion. The measurements are made by monitoring absorption of certain constituents in the longer infrared wavelength region. The long wavelength infrared energy is passed through the finger or other vascularized appendage. The infrared light passing through the finger is measured. The infrared source is pulsed to prevent burning or other patient discomfort. The bursts are also synchronized with the heartbeat so that only two pulses of infrared light are sent through the finger per heartbeat. The detected signals are then analyzed for glucose and other blood constituent information.

U.S. Pat. No. 5,398,681, to Kuperschmidt, shows a device which is said to be a pocket-type apparatus for measurement of blood glucose using a polarized-modulated laser beam. The laser light is introduced into a finger or ear lobe and the phase difference between a reference signal and the measurement signal is measured and processed to formulate and calculate a blood glucose concentration which is then displayed.

U.S. Pat. No. 6,001,067 shows an implantable device suitable for glucose monitoring. It utilizes a membrane which is in contact with a thin electrolyte phase, which in turn is covered by an enzyme-containing membrane, e.g., glucose oxidase in a polymer system. Sensors are positioned in such a way that they measure the electro-chemical reaction of the glucose within the membranes. That information is then passed to the desired source.

None of the cited prior art suggests the device and method of using this device described and claimed below.

SUMMARY OF THE INVENTION

This invention is a glucose level measurement device utilizing IR-ATR spectroscopy and a method of using the device. The inventive device itself is preferably made up of four parts:

a.) an IR source for emitting an IR beam into the ATR plate, b.) the ATR plate against which the sampled human skin surface is pressed, and c.) at least two IR sensors for simultaneously measuring absorbance of two specific regions of the IR spectrum, i.e., a "referencing wavelength" and a "measuring wavelength." The IR source must emit IR radiation at least in the region of the referencing wavelength and the measuring wavelength. For glucose, the referencing wavelength is between about 8.25 micrometers and about 8.75 micrometers and the measuring wavelength is between about 9.50 micrometers and about 10.00 micrometers. The IR sources may be broadband IR sources, non-laser sources, or two or more selected wavelength lasers.

Other analyte materials which have both referencing wavelengths and measuring wavelengths as are described in more detail below and that preferably are found in the outer regions of the skin may be measured using the inventive devices and procedures described herein.

The ATR plate is configured to permit multiple internal reflections, perhaps 3–15 internal reflections or more, against said measurement surface prior to measurement by the IR sensors. Typically the IR beam emitted from the ATR plate is split for the IR sensors using a beam splitter or equivalent optical device. Once the split beams are measured by the IR sensors, the resulting signals are then transformed using analog comparators or digital computers into readable or displayable values.

It is usually important that the device have some accommodation for holding the body part against the ATR plate, preferably at some value which is constant and above a selected minimum pressure.

The method for determining the blood glucose level, using the glucose measurement device, comprises the steps of.

a.) contacting a selected skin surface with the ATR plate, b.) irradiating that human skin surface with an IR beam having components at least in the region of the referencing wavelength and the measuring wavelength, and c.) detecting and quantifying those referencing and said measuring wavelength components in that reflected IR beam.

The procedure ideally includes the further steps of maintaining the skin surface on said ATR plate at an adequate pressure which is both constant and above a selected minimum pressure and, desirably cleaning the skin surface before measurement. A step of actually measuring the pressure may also be included.

A normalizing step practiced by simultaneously detecting and quantifying the referencing and measuring wavelength components prior to contacting the skin surface is also desirable.

A final portion of this invention is a cleaning kit used for cleaning the object skin prior to testing and a process of using that kit. The kit usually is made up of sealed packets, preferably containing absorbent pads, of:

a.) a glucose solvent, e.g., water and/or other highly polar solvent and perhaps containing a weak acid, b.) a solvent for removing the glucose solvent, e.g., isopropanol, and c.) a skin softener or pliability enhancer, e.g., various mineral oils such as "Nujol", not having significant IR wavelength peaks between about 8.25 micrometers and about 8.75 micrometers or between about 9.50 micrometers and about 10.00 micrometers. I prefer to mix components b.) and c.). The solvent for removing the glucose solvent similarly should not have an interfering IR signal which persists after several minutes.

DESCRIPTION OF THE INVENTION

Figure 1A:
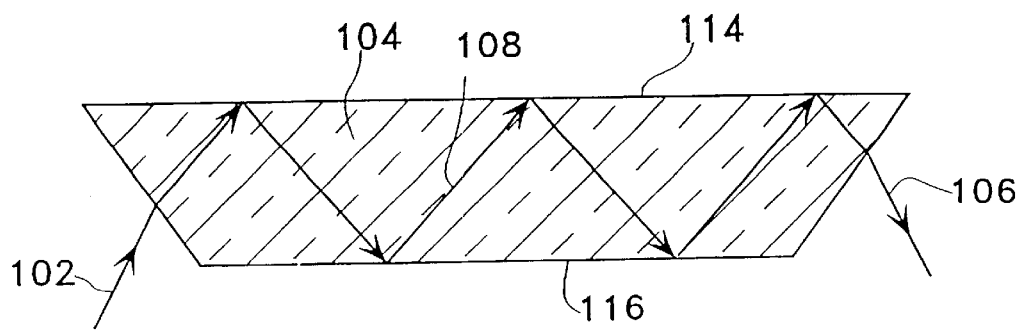
FIGS. 1A, 1B, 1C, and 1D show a side view of various ATR plates and their general operation.
Figure 1B:
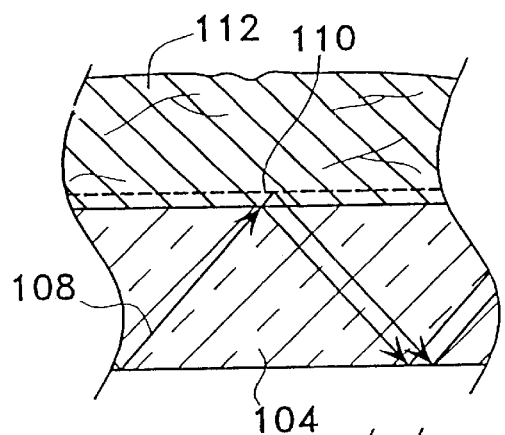

The device in this invention uses infrared ("IR") attenuated total reflectance ("ATR") spectroscopy to detect and ultimately to determine the level of a selected analyte, preferably blood glucose, in the human body. Preferably, the inventive device uses an ATR procedure in which the size and configuration of the crystal permits a number of internal reflections before the beam is allowed to exit the crystal with its measured information. In general, as shown in FIGS. 1A and 1B, when an infrared beam (102) is incident on the upper surface of the ATR crystal (104)—or ATR plate—at an angle which exceeds a critical angle $\Theta_C$, the beam (102) will be completely totally reflected within crystal (104). Each reflection of the beam within the ATR plate, and specifically against the upper surface (114), provides a bit more information about the composition of the sample (112) resting against that upper surface (114). The more numerous the reflections, and the greater the penetration depth of the reflection, the higher is the quality of the information. The incident beam (102) becomes reflected beam (106) as it exits crystal (104) as shown in FIG. 1A. Higher refractive index materials are typically chosen for the ATR crystal to minimize the critical angle. The critical angle is a function of the refractive indices of both the sample and the ATR crystal and is defined as:

$$\Theta_C = \sin^{-1}\left(\frac{n_2}{n_1}\right)$$

Here, $n_1$ is the refractive index of the ATR crystal and $n_2$ is the refractive index of the sample.

Throughout this specification, we refer to wavelength measures as specific values. It should be understood that we intend those values to be bands or ranges of values, typically with a tolerance of +/−0.20 micron, preferably +/−0.10 micron. For instance, a value of 8.25 microns would mean a band of 8.15 to 8.35 microns, and perhaps 8.05 to 8.45 microns depending upon the context.

As shown in FIG. 1B, the internally reflected beam (108) includes an evanescent wave (110) which penetrates a short distance into sample (112) over a wide wavelength range. In those regions of the IR spectrum in which the sample absorbs IR, some portion of the light does not return to the sensor. It is these regions of IR absorbance which provide information, in this inventive device, for quantification of the glucose level.

We have found that the mid-IR spectrum does not penetrate into the skin to an appreciable level. Specifically, the skin is made up of a number of layers: the outermost—the stratum corneum—is a layer substantially free of cholesterol, water, gamma globulin, albumin, and blood. It is a shallow outer region covering the stratum granulosum, the stratum spinosum, and the basal layer. The area between the basal layer to the outside is not vascularized. It is unlikely that any layer other than the stratum corneum is traversed by the mid-IR light involved in this inventive device. Although we do not wish to be bound by theory, it is likely that the eccrine or sweat glands transport the glucose to the outer skin layers for measurement and analysis by our inventions.

We prefer the use of higher refractive index crystals such as zinc selenide, zinc sulfide, diamond, germanium, and silicon as the ATR plate. The index of refraction of the ATR plate (104) should be significantly higher than that of the sample (112).

Figure 1C:
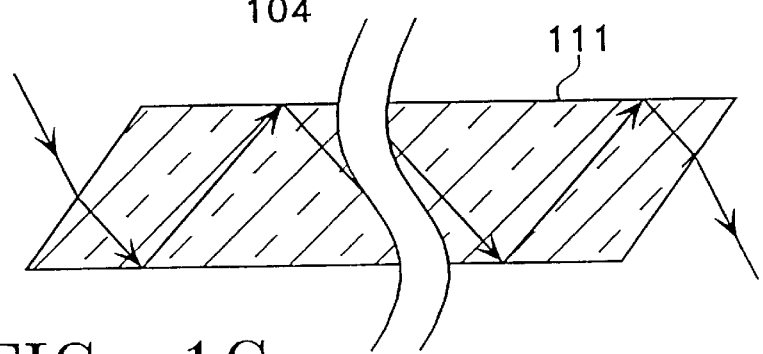
Figure 1D:
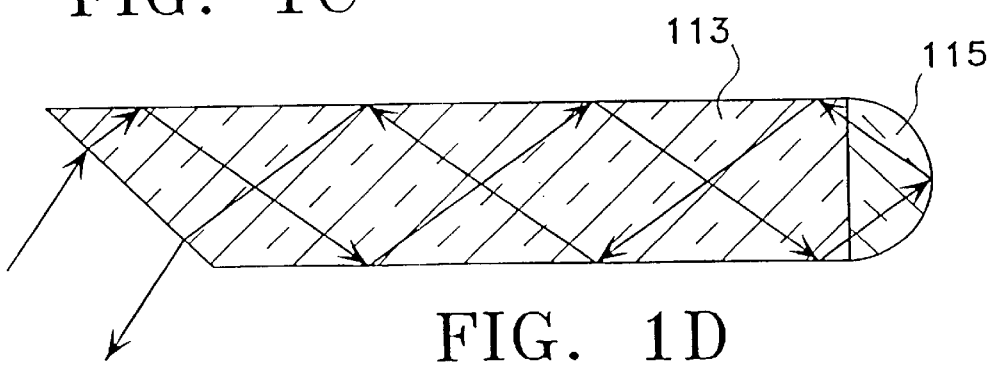

Further, the ATR crystal (104) shown in FIG. 1A is shown to be trapezoidal and having an upper surface (114) for contact with the sample, which sample, in this case, is skin from a living human body. However, this shape is only for the purposes of mechanical convenience and ease of application into a working commercial device. Other shapes, in particular, a parallelogram (111) such as shown in FIG. 1C and the reflective crystal (113) shown in FIG. 1D having mirrored end (115), are also quite suitable for this inventive device should the designer so require. The mirrored reflective crystal (113) has the advantage of, and perhaps the detriment of having both an IR source and the IR sensors at the same end of the crystal.

It is generally essential that the ATR crystal or plate (104) have a sample or upper surface (114) which is essentially parallel to the lower surface (116). In general, the ATR plate (104) is preferably configured and utilized so that the product of the practical number of internal reflections of internal reflected beam (108) and the skin penetration per reflection of this product is maximized. When maximizing this product, called the effective pathlength (EPL), the information level in beam (106) as it leaves ATR plate (104) is significantly higher. Further, the higher the value of the index of refraction, $n_2$, of the ATR plate (104), the higher is the number of internal reflections. The sensitivity of the IR sensors also need not be as high when the EPL is maximized.

We consider the number of total reflections within the crystal to be preferably from 3–15 or more for adequate results.

We have surprisingly found that a glucose measuring device made according to this invention is quite effective on the human skin of the hands and fingers. We have found that the glucose concentration as measured by the inventive devices correlates very closely with the glucose concentration determined by a direct determination from a blood sample. As will be discussed below, the glucose level as measured by the inventive device also is surprisingly found closely to track the glucose level of blood in time as well. This is surprising in that the IR beam likely passes into the skin, i.e., the stratum corneum, for only a few microns. It is unlikely in a fingertip that any blood is crossed by that light path. As discussed above, the stratum corneum is the outer layer of skin and is substantially unvascularized. The stratum corneum is the final outer product of epidermal differentiation or keratinization. It is made up of a number of closely packed layers of flattened polyhedral corneocytes (also known as squames). These cells overlap and interlock with neighboring cells by ridges and grooves. In the thin skin of the human body, this layer may be only a few cells deep, but in thicker skin, such as may be found on the toes and feet, it may be more than 50 cells deep. The plasma membrane of the corneocyte appears thickened compared with that of keratinocytes in the lower layers of the skin, but this apparent deposition of a dense marginal band formed by stabilization of a soluble precursor, involucrin, just below the stratum corneum.

It is sometimes necessary to clean the skin exterior prior before sampling to remove extraneous glucose from the skin surface. When doing so, it is important to select cleaning materials which have IR spectra that do not interfere with the IR spectra of glucose. We consider a kit of the following to be suitable for preparation of the sample skin for the testing. The components are: a.) a glucose solvent, e.g., water or other highly polar solvent; b.) a solvent for removing the water, e.g., isopropanol, and c.) a skin softener or pliability enhancer not having significant IR peaks in the noted IR regions, e.g., mineral oils such as those sold as "Nujol". Preferably the b.) and c.) components are admixed, although they need not be. Certain mixtures of the first two components may be acceptable, but only if the sampling situation is such that the solvents evaporate without spectrographically significant residue. We have also found that soap and its residue are sometimes a problem. Consequently, addition of a weak acid again not having significant IR peaks in the noted IR regions, to the a.) component, i.e., the solvent for removing glucose, is desirable. The preferred weak acid is boric acid. The inventive kit preferably is made up of sealed packets of the components, most preferably each packet containing an absorbent pad.

Figure 2:
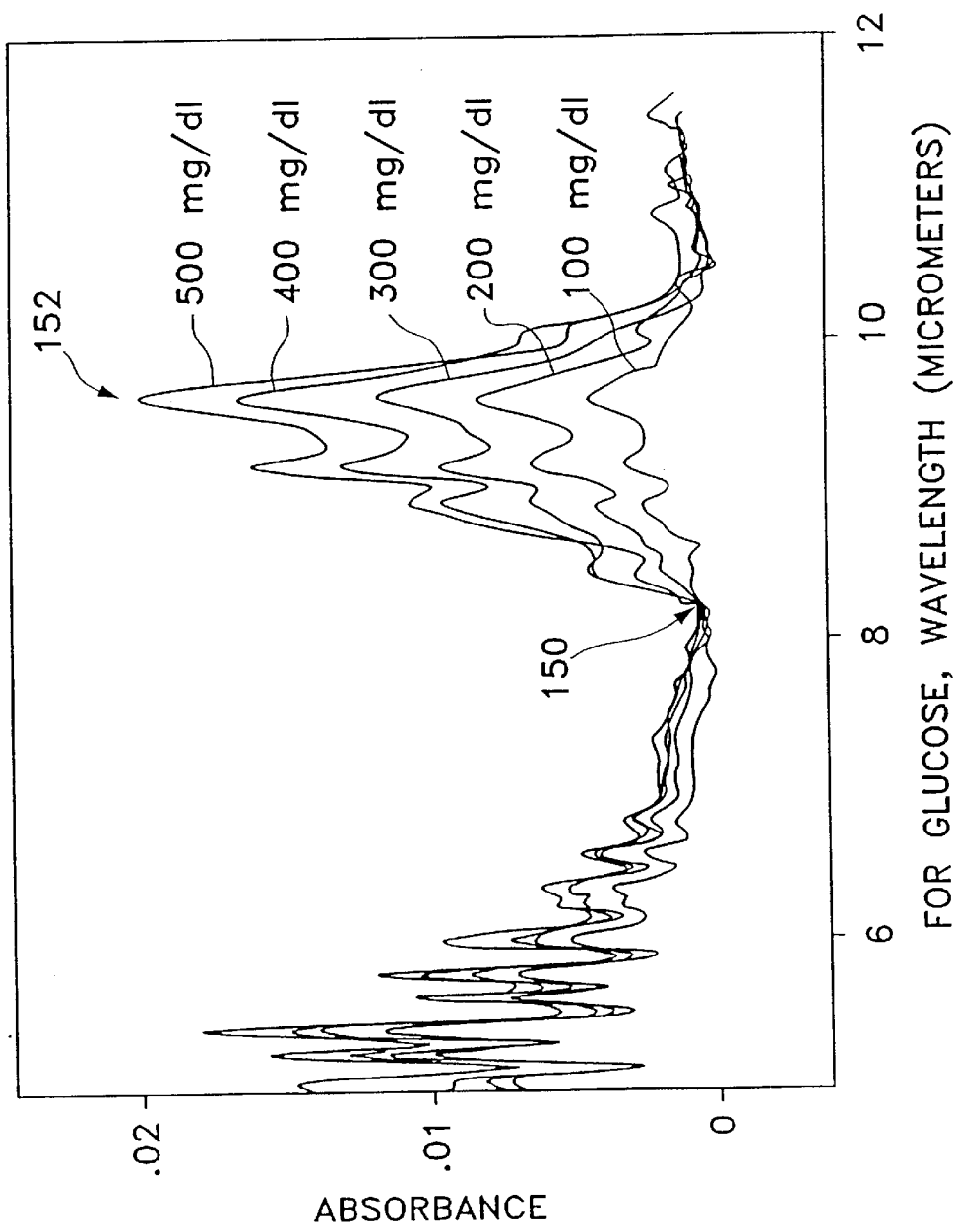
FIG. 2 shows an IR spectrum of d-glucose.

Additionally, the inventive device can be highly simplified compared to other known devices in that the device can be "self-normalizing" due to the specifics of the IR signature of glucose. FIG. 2 shows the IR absorbance spectra of d-glucose. The family of curves there shows that in certain regions of the IR spectrum, there is a correlation between absorbance and the concentration of glucose. Further, there is a region in which the absorbance is not at all dependent upon the concentration of glucose. Our device, in its preferable method of use, uses these two regions of the IR spectra. These regions are in the so-called mid-IR range, i.e., wavelengths between 2.5 and 14 micrometers. In particular, the "referencing wavelength" point is just above 8 micrometers (150), e.g., 8.25 to 8.75 micrometers, and the pronounced peaks (152) at the region between about 9.50 and 10.00 micrometers is used as a "measuring wavelength". The family of peaks (152) may be used to determine the desired-glucose concentration.

Use of the two noted IR regions is also particularly suitable since other components typically found in the skin, e.g., water, cholesterol, etc., do not cause significant measurement error when using the method described herein.

Figure 3:
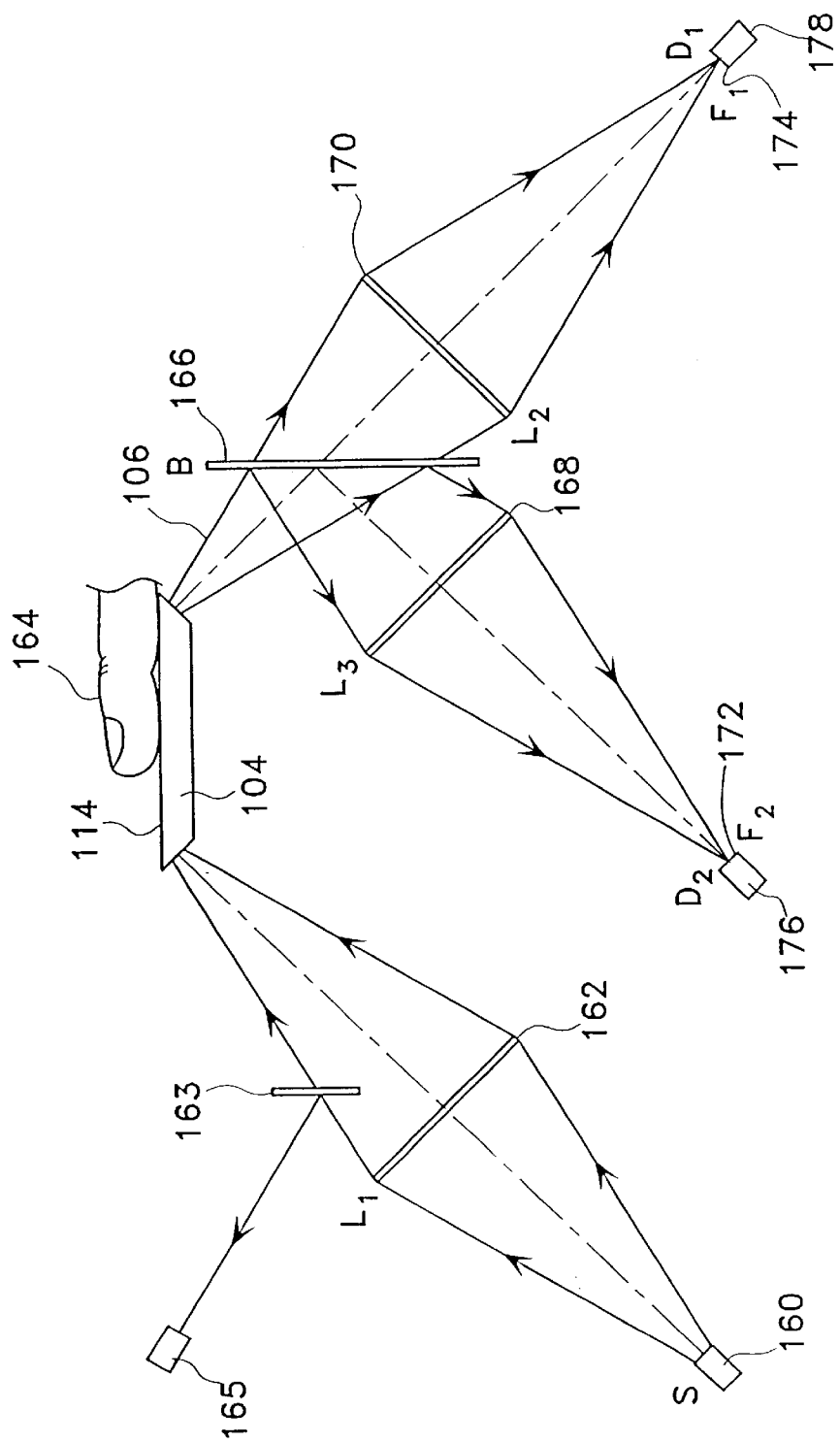
FIG. 3 shows a schematicized layout of the optics of the inventive device.

FIG. 3 shows an optical schematic of a desired variation of the inventive device. ATR crystal (104) with sample side (114) is shown and IR source (160) is provided. IR source (160) may be any of a variety of different kinds of sources. It may be a broadband IR source, one having radiant temperatures of 300° C. to 800° C., or a pair of IR lasers selected for the two regions of measurement discussed above, or other suitably emitted or filtered IR light sources. A single laser may not be a preferred light source in that a laser is a single wavelength source and the preferred operation of this device requires light sources simultaneously emitting two IR wavelengths. Lens (162), for focusing light from IR source (160) into ATR plate (104), is also shown. It may be desirable to include an additional mirror (163) to intercept a portion of the beam before it enters the ATR plate (104) and then to measure the strength of that beam in IR sensor (165). Measurement of that incident light strength (during normalization and during the sample measurement) assures that any changes in that value can be compensated for.

The light then passes into ATR plate (104) for contact with body part (164), shown in this instance to be the desired finger. The reflected beam (106) exits ATR plate (104) and is then desirably split using beam splitter (166). Beam splitter (166) simply transmits some portion of the light through the splitter and reflects the remainder. The two beams may then be passed through, respectively, lenses (168) and (170). The so-focussed beams are then passed to a pair of sensors which are specifically selected for detecting and measuring the magnitude of the two beams in the selected IR regions. Generally, the sensors will be made up of filters (172) and (174) with light sensors (176) and (178) behind. Generally, one of the filters (172), (174) will be in the region of the referencing wavelength and the other will be in that of the measuring wavelength.

Figure 4:
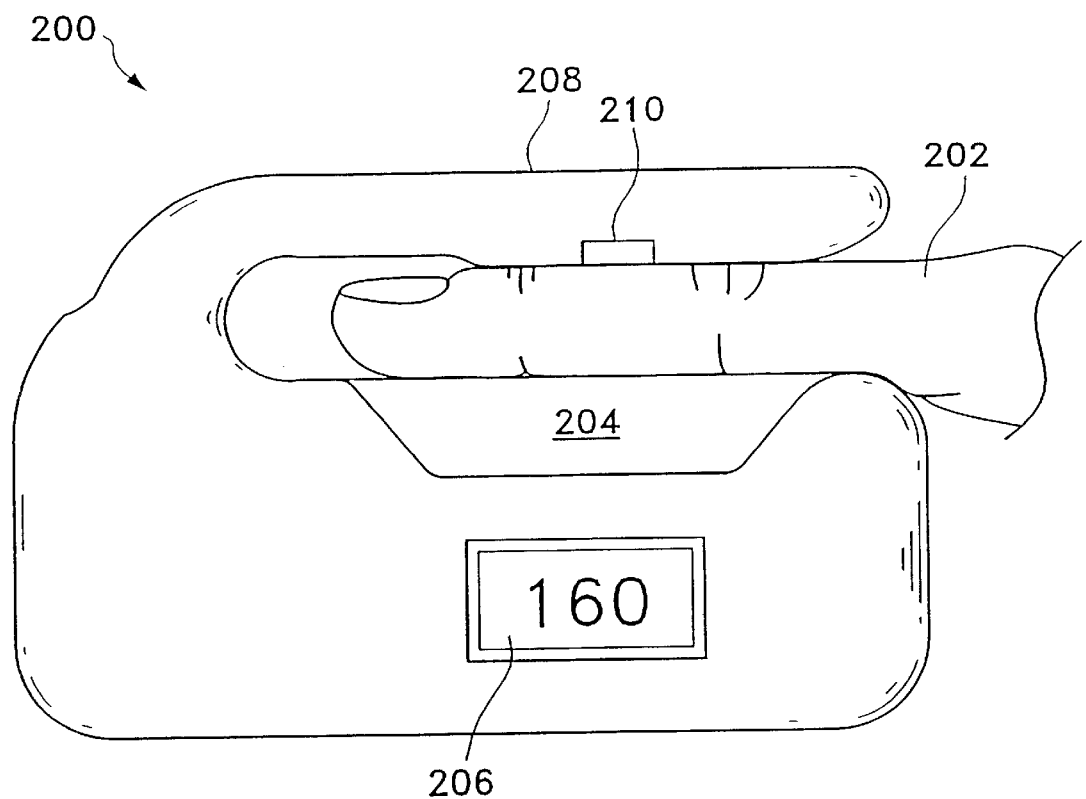
FIG. 4 shows a packaged variation of the inventive glucose measuring device.

FIG. 4 shows perhaps a variation of this device (200) showing the finger of the user (202) over the ATR plate (204) with a display (206). Further shown in this desirable variation (200) is a pressure maintaining component (208). We have found that is very highly desirable to maintain a minimum threshold pressure on the body part which is to be used as the area to be measured. Generally, a variance in the pressure does not shift the position of the detected IR spectra, but it may affect the sensitivity of the overall device. Although it is possible to teach the user to press hard enough on the device to reach the minimum threshold pressure, we have determined for each design of the device it is much more appropriate that the design of a particular variation of the inventive device be designed with a specific sample pressure in mind. The appropriate pressure will vary with, e.g., the size of the ATR plate and the like. A constant pressure above that minimum threshold value is most desired.

The variation shown in FIG. 4 uses a simple component arm (208) to maintain pressure of the finger (202) on ATR plate (204). Other variations within the scope of this invention may include clamps and the like.

It should be apparent that once an appropriate pressure is determined for a specific design, the inventive device may include a pressure sensor, e.g., (210) as is shown in FIG. 4, to measure adherence to that minimum pressure. Pressure sensor (210) may alternatively be placed beneath ATR plate (204). It is envisioned that normally a pressure sensor such as (210) would provide an output signal which would provide a "no-go/go" type of signal to the user.

Figure 5:
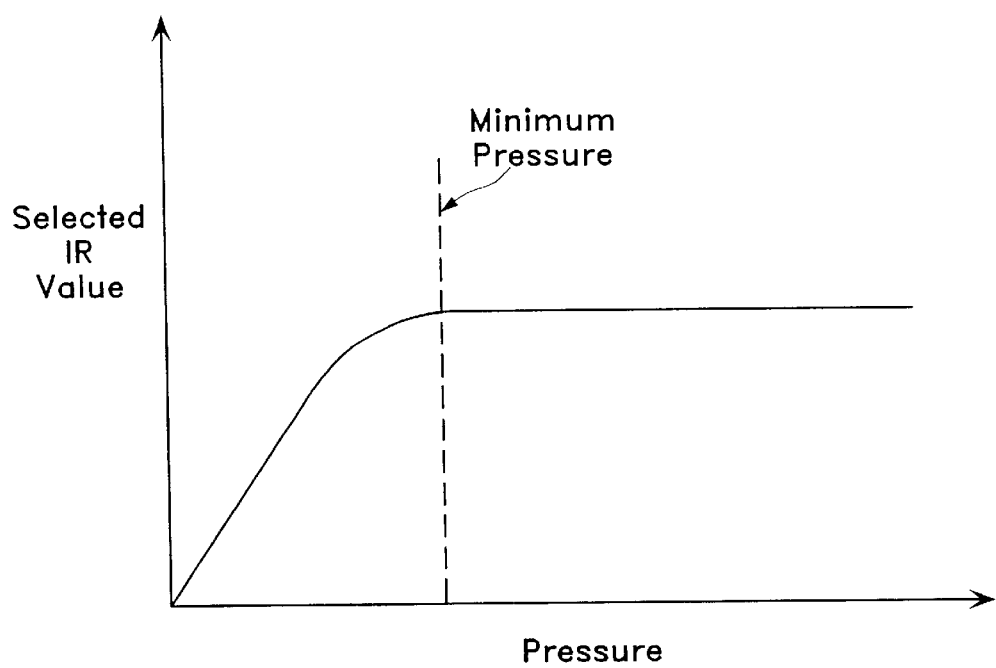
FIG. 5 shows a graph of pressure on the ATR crystal vs. IR value.

Further, as shown in FIG. 5, the appropriate pressure may be achieved when using our device simply by increasing the pressure of the body part on the ATR crystal surface until a selected, measured IR value becomes constant.

Method of Use

In general, the inventive device described above is used in the following manner: a skin surface on a human being, for instance, the skin of the finger, is placed on the ATR plate. The skin surface is radiated with an IR beam having components at least in the two IR regions we describe above as the "referencing wavelength" and the "measuring wavelength." The beam which ultimately is reflected out of the ATR plate then contains information indicative of the blood glucose level in the user. As noted above, it is also desirable to maintain that skin surface on the ATR plate at a relatively constant pressure that is typically above a selected minimum pressure. This may be done manually or by measuring and maintaining the pressure or monitoring the constancy of a selected IR value.

Typically, the beam leaving the ATR plate is split using an optical beam splitter into at least two beams. Each of the two beams may be then focussed onto its own IR sensor. Each such IR sensor has a specific filter. This is to say that, for instance, one IR sensor may have a filter which removes all light which is not in the region of the referencing wavelength and the other IR sensor would have a filter which remove all wavelengths other than those in the region of the measuring wavelength. As noted above, for glucose, the referencing wavelength is typically in the range of about 8.25 to 8.75 micrometers. For glucose, the measuring wavelength is typically between about 9.5 and 10.0 micrometers.

Other analyte materials which have both referencing wavelengths and measuring wavelengths in the mid-IR range and that are found in the outer regions of the skin may also be measured using the inventive devices and procedures described herein.

Respective signals may be compared using analog or digital computer devices. The signals are then used to calculate analyte values such as blood glucose concentration using various stored calibration values, typically those which are discussed below. The resulting calculated values may then be displayed.

As noted above, it is also desirable both to clean the plate before use and to clean the exterior surface of the skin to be sampled. Again, we have found, for instance in the early morning that the exterior skin is highly loaded with glucose which is easily removed preferably by using the skin preparation kit, or, less preferably, by washing the hands. Reproducible and accurate glucose measurements may then be had in a period as short as ten minutes after cleaning the area of the skin to be measured.

We also note that, depending upon the design of a specific variation of a device made according to the invention, periodic at least an initial calibration of the device, using typical blood sample glucose determinations, may be necessary or desirable.

Determination of blood glucose level from the information provided in the IR spectra is straightforward. A baseline is first determined by measuring the level of infrared absorbance at the measuring and referencing wavelengths, without a sample being present on the sample plate. The skin is then placed in contact with the ATR plate and the two specified absorbance values are again measured. Using these four values, the following calculation is then made.

$$A_1 = \ln\left(\frac{T_{01}}{T_1}\right) = A_{g1} + A_{b1} \quad \text{(Absorbance at referencing spectral band.)}$$

$$A_2 = \ln\left(\frac{T_{02}}{T_2}\right) = A_{g2} + A_{b2} \quad \text{(Absorbance at measuring spectral band.)}$$

where:

$T_{01}$=measured value at reference spectral band w/o sample $T_{02}$=measured value at measuring spectral band w/o sample $T_1$=measured value at reference spectral band w/ sample $T_2$=measured value at measuring spectral band w/ sample $A_{g1}$=absorbance of glucose at reference spectral band $A_{g2}$=absorbance of glucose at measuring spectral band $A_{b1}$=absorbance of background at reference spectral band $A_{b2}$=absorbance of background at measuring spectral band d=effective path length through the sample.

$a_2$=specific absorptivity at measuring spectral band k=calibration constant for the device $C_g$=measured concentration of glucose Since the background base values are approximately equal (i.e., $A_{b1}=A_{b2}$) and $A_{g1}=0$, then:

$$A_2-A_1=A_{g2}=a_2 d C_g$$

and $$C_g=k(A_2-A_1)$$

The value of $C_g$ is the desired result of this procedure.

Figure 7:
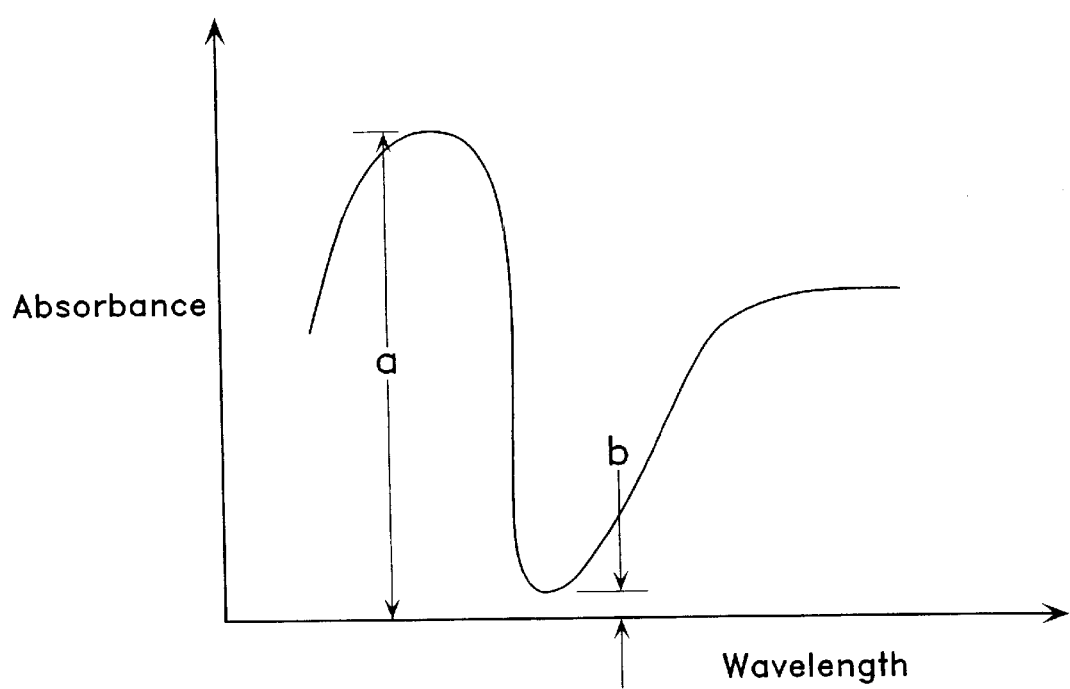
FIG. 7 shows a graph using a transmittance trough as the referencing wavelength.

Similarly, FIG. 7 shows a graph in which the value of the analyte is assessed using similar calculations but in which the "referencing wavelength" is an absorbance trough ("b") unaffected by the concentration of the analyte. The "measuring wavelength" peak ("a") is measured against a baseline.

EXAMPLES

Example 1

Using a commercially available IR spectrometer (Nicolet 510) having a ZnSe crystal ATR plate (55 mm long, 10 mm wide, and 4 mm thick) we tested the inventive procedure. We calibrated the output of the spectrometer by comparing the IR signal to the values actually measured using one of the inventor's blood samples. The inventor used a blood stick known as "Whisper Soft" by Amira Medical Co. and "Glucometer Elite" blood glucose test strips sold by Bayer Corp. of Elkhart, Ind. On each of the various test days, the inventor took several test sticks and measured the glucose value of the resulting blood; the IR test was made at the same approximate time.

Figure 6:
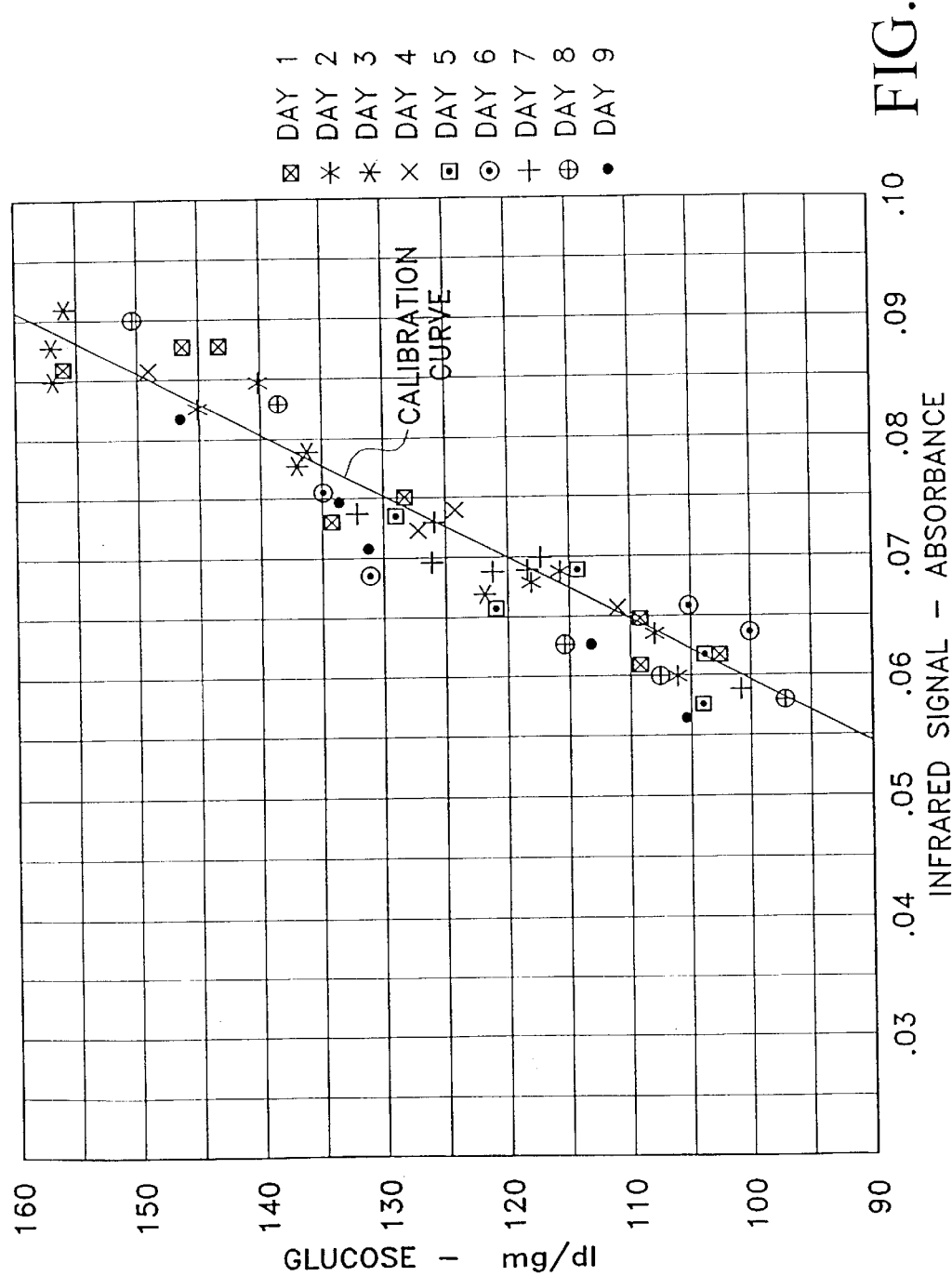
FIG. 6 shows a graph correlating glucose levels measured using a specific variation of the device with glucose levels in the blood determined using a commercial device.

As shown in the calibration curve of FIG. 6, the data are quite consistent. So, where the blood glucose concentration "B" is in (mg/dl) and "S" is the difference between the absorbance at the referencing region and the measuring region as measured by the spectrometer:

$$B=[(1950)\cdot S]-(17).$$

Example 2

Figure 8:
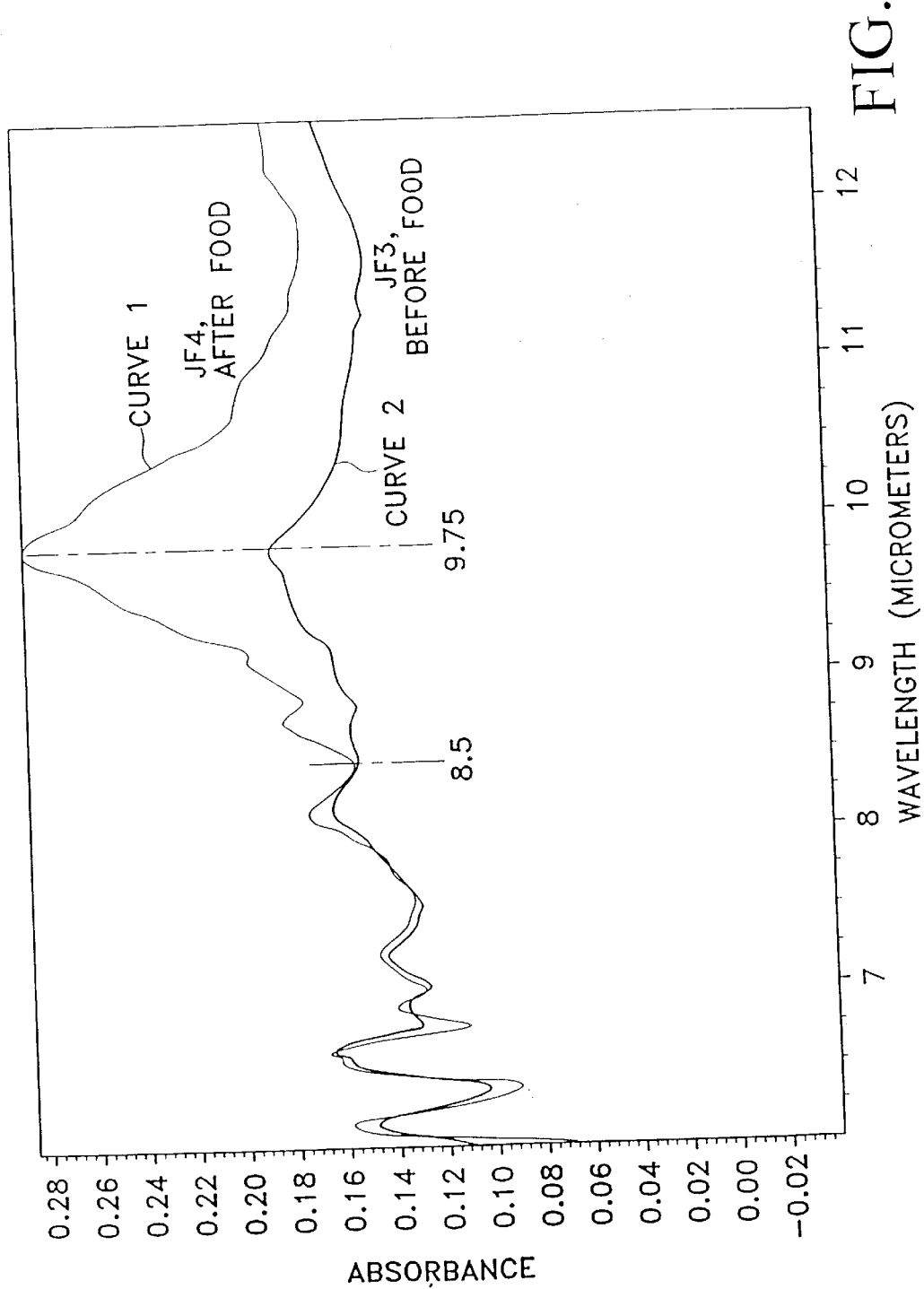
FIG. 8 shows a pair of glucose IR curves (taken before and after eating) for an individual having diabetes made using the inventive glucose measuring device.

In accordance with a clinical protocol, a diabetic was then tested. Curve 1 in FIG. 8 shows the IR absorbance spectrum of the test subject's finger before eating (and after fasting overnight) and curve 2 shows IR absorbance spectrum of the same individual after having eaten. Incidentally, insulin was administered shortly after the measurement of curve 2.

In any event, the significant difference in the two peak heights at the 9.75 micrometer wavelength and the equality of the two IR absorbance values at the 8.50 micrometer value shows the effectiveness of the procedure in measuring glucose level.

Example 3

Figure 9:
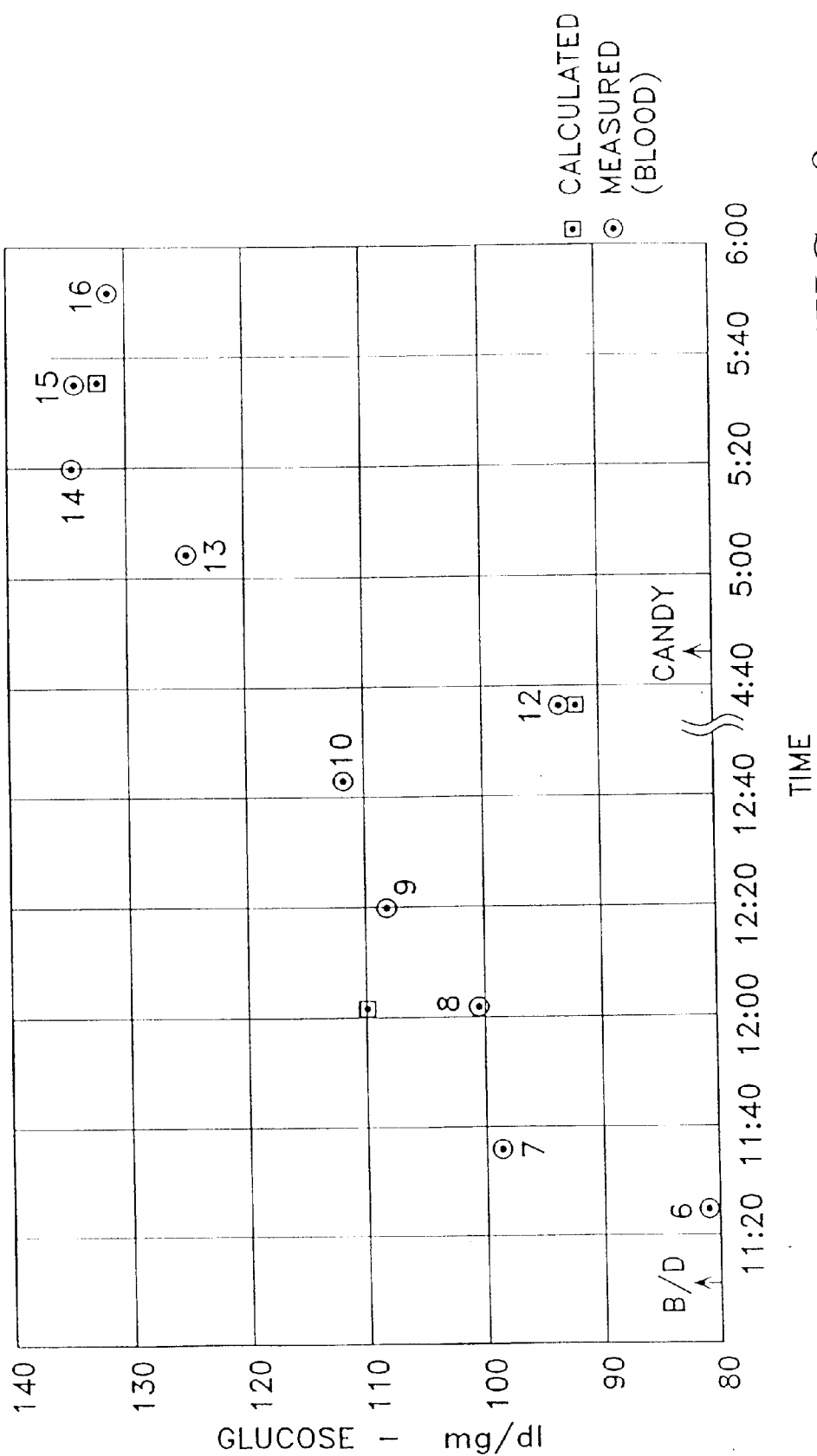
FIG. 9 shows a graph comparing glucose levels in a non-diabetic individual (taken before and after eating) made using the inventive glucose measuring device and direct blood measurement. This graph shows that the inventive procedure tracks blood glucose levels with minimum time lag.

That the inventive glucose monitoring device non-invasively determines blood glucose level and quickly follows changes in that blood glucose level is shown in FIG. 9. Using both the inventive procedure and a commercial glucose device, one of the inventors followed his glucose level for a single day. The blood sticks are considered to be accurate within 15% of the actual reading.

The results are shown in FIG. 9. Of particular interest is the measurement just before 4:40 pm wherein the two values are essentially the same. A high sugar candy bar was eaten at about 4:45 pm and measurements of glucose level were taken using the inventive procedure at about 5:03, 5:18, 5:35 and 5:50. A blood sample was taken at 5:35 and reflected almost the same value as that measured using the inventive procedure. Consequently, the procedure tracks that measured by the blood very quickly.

This invention has been described and specific examples of the invention have been portrayed. The use of those specifics is not intended to limit the invention in any way. Additionally, to the extent there are variations of the invention with are within the spirit of the disclosure and yet are equivalent to the inventions found in the claims, it is our intent that this patent will cover those variations as well.

We claim as our invention:

1. A method for determining the blood glucose level of a human being having skin with a skin surface, comprising the acts of:
   a.) irradiating said skin surface with light containing at least an IR component so to produce a reflected IR beam from said skin surface indicative of said blood glucose level,
   b.) detecting said reflected IR beam, and
   c.) calculating said blood glucose level based solely on said reflected IR beam.

2. The method of claim 1, including repeating acts a.), b.), and c.) until a consistent glucose level reading is obtained.

3. The method of claim 1, wherein said IR component contains mid-IR wavelengths.

4. The method of claim 1, further comprising an act of maintaining said skin surface against an ATR plate at an adequate pressure during the act of irradiating said skin surface with light containing at least an IR component so to produce a reflected IR beam from said skin surface indicative of said blood glucose level.

5. The method of claim 1, wherein said IR component further comprises a referencing wavelength and a measuring wavelength.

6. The method of claim 5, wherein said referencing wavelength is between about 8.25 μm and about 8.1 μm.

7. The method of claim 5, wherein said measuring wavelength is between about 9.50 μm and about 10.00 μm.

8. The method of claim 5, wherein said act of calculating said blood glucose level comprises an act of comparing an absorbance of said reflected IR beam at said referencing wavelength and said measuring wavelength.

9. The method of claim 8, wherein said act of comparing is done with a digital computer.

10. The method of claim 9, further comprising an act of providing a digital signal indicative of blood glucose concentration.

11. The method of claim 1, wherein said act of detecting further comprises an act of absorbing said reflected IR beam with at least two IR sensors.

12. The method of claim 1, wherein said act of calculating said blood glucose level further comprises calculating using stored calibration constants.

* * * * *

UNITED STATES PATENT AND TRADEMARK OFFICE
CERTIFICATE OF CORRECTION

PATENT NO.    : 6,424,849 B1
DATED         : July 23, 2002
INVENTOR(S)   : Herbert L. Berman and Jeffrey N. Roe It is certified that error appears in the above-identified patent and that said Letters Patent is hereby corrected as shown below:

Column 12,
Line 65, please replace "8.1" with -- 8.75 --.

Signed and Sealed this

Twelfth Day of November, 2002

Attest:

JAMES E. ROGAN
Attesting Officer    Director of the United States Patent and Trademark Office